United States Patent [19]
Foreman

[11] Patent Number: 5,441,985
[45] Date of Patent: Aug. 15, 1995

[54] TREATMENT OF LOWER URINARY TRACT DISORDERS WITH SELECTIVE NOREPINEPHRINE UPTAKE INHIBITORS

[75] Inventor: Mark M. Foreman, Indianapolis, Ind.

[73] Assignee: Eli Lilly and Company, Indianapolis, Ind.

[21] Appl. No.: 61,335

[22] Filed: May 13, 1993

Related U.S. Application Data

[63] Continuation of Ser. No. 660,767, Feb. 25, 1991, abandoned.

[51] Int. Cl.⁶ ............................................. A61K 31/135
[52] U.S. Cl. ....................................................... 514/646
[58] Field of Search ............................................ 514/646

[56] References Cited

U.S. PATENT DOCUMENTS

| | | | |
|---|---|---|---|
| 4,314,081 | 2/1982 | Molloy et al. | 564/347 |
| 4,956,388 | 9/1990 | Robertson et al. | 514/651 |

FOREIGN PATENT DOCUMENTS

| | | | |
|---|---|---|---|
| 052492 | 5/1982 | European Pat. Off. | C07C 93/06 |
| 288188 | 10/1988 | European Pat. Off. | C07C 93/00 |
| 367040 | 5/1990 | European Pat. Off. | C07C 233/78 |

OTHER PUBLICATIONS

Wong et al., *J. Pharmacology and Experimental Therapeutics*, 222(1), 61–65 (1982).
*The Merck Manual* pp. 1639–1641, published by Merck & Co., Inc., Rahway, N.J. 1985.
Rushton, *J. Pediatrics*, 114(2), 691–696 (1989).
Shaffer et al., *Neuropharm.*, 18, 33 (1979).
Lipshultz et al., *Invest. Urology*, 11, 182 (1973).
Khanna et al., *Urology*, 6, 48 (1975).
Zerbe et al., *J. Pharmacol. Ex. Ther.*, 232(1), 139–143 (1985).
Bertilsson et al., *Clin. Pharmacol. Ther.*, 40(3), 261–267 (1986).
Cohen et al., *J. Pharmacol. Exp. Ther.*, 248(3), 1063–1068 (1989).
Goodman et al., *Pharmacological Basis of Therapeutics* 7th ed., Macmillan Pub. Co., New York Apr. 1989.

*Primary Examiner*—Marianne M. Cintins
*Assistant Examiner*—Keith MacMillan
*Attorney, Agent, or Firm*—Joseph A. Jones; Robert A. Conrad

[57] ABSTRACT

This invention provides a method of treating lower urinary tract disorders in mammals employing compounds which inhibit norepinephrine reuptake and having negligible anticholinergic effect.

13 Claims, No Drawings

TREATMENT OF LOWER URINARY TRACT DISORDERS WITH SELECTIVE NOREPINEPHRINE UPTAKE INHIBITORS

This application is a continuation of application Ser. No. 07/660,767, filed on Feb. 25, 1991, now abandoned.

BACKGROUND OF THE INVENTION

The present invention provides for the treatment of lower urinary tract disorders such as urinary incontinence, detrusor instability and interstitial cystitis using agents that suppress norepinephrine uptake activity but do not have the undesirable side effects due to anti-cholinergic activity possessed by current treatments.

Urinary incontinence is generally defined as the involuntary loss of urine and is most common in four groups of patients including children, women, elderly, and neurologic disease patients. Detrusor instability is characterized by spasmodic bladder contractions or bladder contractions elicited by small volumes, and is often accompanied by incontinence and urinary frequency. Interstitial cystitis is an idiopathic pelvic pain syndrome which can also include detrusor instability as a component of its pathology.

Nocturnal enuresis is classified as an involuntary micturition during sleep after 5 years of age and may exist in either primary or secondary forms. The diagnosis of primary nocturnal enuresis is made if the patient has never developed voluntary control of micturition during sleep. The diagnosis of secondary nocturnal enuresis is made if the patient has had transient periods of micturition control during sleep. Nocturnal enuresis occurs in 30% of all children at 4 years of age, 10% at 6 years, 3% at 10 years and 1% at 18 years. Secondary nocturnal enuresis accounts for approximately 20-25% of the pediatric enurenic cases. Although some enuretic children also have diurnal enuresis, over 80% of the enuretic children have exclusively nocturnal enuresis.

The predominant types of incontinence in women are stress and urge incontinence. Stress incontinence is the involuntary loss of urine through an intact urethra produced during times of increased abdominal pressure such as during physical activity and coughing. This implies that the urethra cannot generate sufficient pressure for outlet resistance to compensate for increases in intrabladder pressure. This loss of urine is not accompanied by premonitory sensations of the need to void and is not related to the fullness of the bladder. Urge incontinence is the involuntary loss of urine through an intact urethra due to an increased intrabladder pressure. In contrast to stress incontinence, urge incontinence is caused by an episodic bladder contraction (detrusor instability) which exceeds the outlet resistance pressure generated by the urethra and is accompanied by a perception of urgency to void.

Stress incontinence is the most common form of incontinence in young women. In two longitudinal studies, pure stress incontinence was found to occur in 15-22% of women from ages 17-75+. The highest incidence of stress incontinence (25-30%) occurs at 25-45 years of age or during the childbearing years. Following the first child birth, the overall incidence and incidence of severe stress incontinence doubles. However, 35-50% of nulliparous women have also occasional stress incontinence. In a study of nulliparous nursing students between the ages of 17-24 years, daily stress incontinence was reported in 17% of the women.

Urge incontinence occurs in approximately 10% of women from ages 17-75+ years and increases progressively with age. In addition to stress or urge incontinence, 7-14% of women from ages 17-75+ years of age have characteristics of both urge and stress incontinence. The incidence of this "complex incontinence" doubles during the childbearing years and ranges from 13-28% from ages 17 to 75+ years of age.

The types of incontinence seen in the elderly include urge incontinence (detrusor instability), stress incontinence, complex incontinence (urge and stress incontinence) and total incontinence. Urge incontinence is the most common form of incontinence in the elderly men and women and is caused by abnormal neuromuscular responses of the bladder. Following urge incontinence in incidence are complex, stress, overflow and total incontinence, respectively. Stress incontinence is relatively rare in elderly men but common in women. Stress incontinence ,is caused by pelvic surgery, anatomical changes in the orientation of the bladder and urethra, decreased tone of the pelvic muscles, deterioration of the urethra following the cessation of estrogen secretion, and idiopathic decrease in the neuromuscular response of tile urethra. Overflow incontinence is due to an overfilling and distension of an areflexic bladder which exceeds the urethral resistance. Total incontinence is associated with dementia and sphincter or nerve damage.

In addition to the types of incontinence described above, urge incontinence is also associated with neurologic disorders such as multiple sclerosis, Alzheimer's disease and Parkinson's disease. This urge incontinence caused by neurologic disorders result from bladder hyperactivity. The incidence of incontinence in multiple sclerosis patients has been estimated to be 60-90%. Urinary incontinence is among the early neurologic symptoms of Parkinson's disease patients and is frequently exacerbated by treatment with anti-Parkinson drugs.

Interstitial cystitis is a syndrome that is characterized by increases in urination frequency, urgency, suprapubic pressure and pain with bladder filling. This syndrome is not associated with infections or cytological damage. The average age at onset of this disorder is 40-50 years. The quality of life is considered to be worse than that of end stage renal disease. According to the NIH report on interstitial cystitis, there are 20,000 to 90,000 diagnosed cases of this disorder in United States and the upper boundary for undiagnosed cases is 4-5 times larger than the range of diagnosed cases. This disorder has increased in awareness in the urologic community due to the formation of the American Interstitial Cystitis Association.

The treatments for incontinence vary with the particular type. For example, with no therapy, the spontaneous cure rate for nocturnal enuresis is approximately 15% per year. The success rate for nonpharmacologic therapies such as motivational counseling, bladder exercises and enuresis alarms ranges from 25-70%. The tricyclic antidepressants have been the most effective pharmacologic agents for treating nocturnal enuresis. Imipramine is the most widely used agent; however other tricyclics such as nortriptyline, amitriptyline, and desipramine are also effective. Enuresis can be cured in over 50% of patients following treatment with imipramine and improvements can be seen in another 15-20%. A successful response to this therapy is usually seen in the first week of therapy and often after the first dose.

The best results are seen in children with normal sized bladders who are occasionally continent at night. The worst results are seen in children with small bladders and in older adolescents. This therapy, however, does have toxic risks. The tricyclic anti-depressants in general, and imipramine in particular, are not approved for use in children under 5 years of age as these compounds are particularly toxic and potentially lethal in low dosage. Other pharmacologic therapies include the use of oxybutynin, antispasmotic agent that reduces uninhibited detrusor muscles contractions, and the antidiuretic agent desmopressin.

The predominant forms of therapy for incontinent women include a variety of surgical procedures that attempt to resuspend the bladder and/or reinforce the urethra; pelvic floor exercises; and pharmacologic therapies. Imipramine is effective as a single therapy in restoring continence to women with stress incontinence. The efficacy of imipramine in urge incontinence has varied along clinical studies and appears greater when used as a combination therapy with anticholinergic and antispasmotic agents.

Nonpharmacologic therapies for incontinence in the elderly include behavior modification, absorptive pads, catheterization and surgery. Pharmacologic therapies for stress incontinence are aimed at increasing internal sphincter tone through increasing alpha adrenergic receptor stimulation. The most common agents used are tricyclic antidepressants, ephedrine, and phenylpropanolamine. Estrogen is also used as a component in this therapy for women in order to reverse or reduce the deterioration of the genitoulinary tracts following cessation of estrogen secretion. Pharmacologic therapies for urge incontinence are aimed at suppressing episodic bladder contractions and includes agents such as propantheline, oxybutynin, and imipramine.

Nonpharmacologic therapies of interstitial cystitis include hydrodistension of the bladder during anesthesia and in extreme cases removal of the bladder with bladder reconstruction from segments of the bowel. Pharmacologic therapies include the use of dimethylsulfoxide or sodium pentosanpolysulfate by intravesicular administration and the use of tricyclic antidepressants, such as amitriptyline or desipramine. The intravesicular therapies are designed to desensitize the bladder wall, whereas the tricyclic antidepressants are used to alter the central thresholds for pain and alter bladder function.

Tricyclic antidepressants such as imipramine are among the most widely prescribed drugs for the treatment of incontinence in children, women, and elderly patients. Their effects are to decrease bladder pressure and decrease output resistance by increasing urethral pressure. As noted above, however, the urologic uses of imipramine and other tricyclic anti-depressants are limited by significant side effects due to their anti-cholinergic activities. In particular such side effects include dry mouth, constipation, drowsiness, tremors, dizziness, and excess sweating. Moreover, as noted above, the use of the tricyclics for the treatment of children is limited due to their potential toxicity.

Because its common use for the treatment of incontinence, imipramine has been the most fully studied agent for this utility. There have been at least five different proposed mechanisms that have been suggested as the basis for its effect for treating incontinence.

Imipramine has been demonstrated to have anticholinergic activity. In a series of in vitro studies with guinea pig bladder strips and in vivo bladder cystometrogram studies in guinea pigs, imipramine had anticholinergic, antispasmodic, and local anesthetic activity. (Noronha-Blob, et al., *J. Pharm. Exp. Ther.*, 251,586 (1989)). Imipramine induced a 50% suppression of field stimulated and bethanechol-induced contraction in a rabbit bladder organ bath preparation. Atropine induced a 70% relaxation of bethanechol-induced contraction and a 30% inhibition of field stimulated contractions and verapamil induced a 85 and 81% inhibition of bethanechol and field stimulated contractions, respectively. (Kato, et al., *J. Urol.*, 141, 1471 (1989)).

Imipramine was shown to block in vitro contractile responses of rabbit, dog, and human bladder strips to acetylcholine (ACH) (Labay and Boyarsky, *J. Urol.*, 109, 385 (1973); Labay, et al., *Arch. Phys. Med. Rehabil.*, 55, 166 (1974)). Imipramine also suppressed cholinergic contractile responses in dog bladder strips induced by bethanechol. The authors concluded that imipramine has anticholinergic effects (Benson, et al., *Urology*, 9, 31 (1977)). Imipramine also reduced bladder pressure responses in female dogs to pelvic nerve stimulation. The authors concluded these effects are "compatible with parasympatholytic activity". (Gregory, et al., *Invest. Urol.*, 12, 233 (1974)). Somogyi, et al. (Society for Neurosciences Meeting-1989, Abstract #326.5) recently studied the effect of imipramine on the release of norepinephrine from rat bladder tissue in vitro and concluded that the "strong antagonistic effect on muscarinic presynaptic receptors" was an "action which very likely contributes to the therapeutic effects of the drug". Imipramine has an $IC_{50}$ for displacement of tritiated-quinuclidinol benzoate (QNB) binding in bladder homogenates of 13.0 $\mu$M compared to 52.0, 29.5 and 1.4 $\mu$M for atropine, propantheline, and oxybutynin, respectively. (Levin, et al., *J. Urol.*, 128, 396 (1982)). QNB is a radioligand for cholinergic receptors.

Imipramine has also been shown to affect calcium channel blockade. Olubadewo (*Arch. Int. Pharmacodyn.*, 245, 84 (1980)) found that imipramine inhibited both $Ca^{+2}$ and carbachol-induced contractions, which would indicate anticholinergic and calcium channel blockade effects. The authors stated that "On the basis of these evidences and literature reports, it was concluded that imipramine does not principally control enuresis through an effect on either the cholinergic or the adrenergic influence on bladder function." A decreased effectiveness of calcium to augment bethanechol-induced contraction of rabbit bladder strips was observed in the presence of imipramine. (Malkowicz, et al,, *J. Urol.*, 138, 667 (1987)). The tricyclic antidepressants amitriptyline and desipramine suppressed the contractile response of rat urinary bladder strips to electrical stimulation. This effect was augmented in media with reduced calcium concentration and suppressed in media with elevated calcium concentration. The tricyclics also augment the effects of atropine. The author concluded that the effects of these tricyclics are related to the interference with calcium movement resulting in direct membrane relaxation and that these agents also have anticholinergic activity. (Akah, *Arch. Int. Pharmacodyn.*, 284, 231 (1986)). Imipramine also induced a suppression of field stimulated and bethanechol-induced contraction in a rabbit bladder organ bath preparation (Kato, et al., supra).

Imipramine has also been shown to possess local anesthetic activity. In addition to the article by Noronha-Blob, et al., supra, imipramine was found to antagonize carbamylcholine and barium chloride-induced contractions of rabbit detrusor strips in vitro and to block the impulse conduction of frog sciatic nerves in vitro. Since imipramine suppressed responses in all of these models, the authors concluded that "imipramine is shown to exert appreciable noncompetitive antagonism of both carbamylcholine-induced and BaCl$_2$-induced detrusor spasms, as well as potent local anesthetic activity." (Fredericks, et al., *Urology*, 12, 487 (1978)). Imipramine was also shown to reduce in vitro contractile response to electrical stimulation. The author attributed "the powerful blocking effect of imipramine to its procaine-like action at the nerve terminals and the adjacent effector cell membrane". (Dhattiwala, *J. Pharm. Pharmac.*, 28. 453 (1976)). Imipramine also suppressed contractile responses to barium chloride indicating that it has anti-spasmotic activity. (Benson, et al., *Urology*, 9, 31 (1977)). The authors state in their conclusions that "the mode of action of imipramine on the urinary bladder has been subject of much recent work and of much controversy. Many pathways have been proposed: (1) a central anti.-depressant effect, (2) a peripheral cholinergic receptor blockade, (3) a peripheral sympathomimetic effect via a cocaine-like blocking of nerve terminal reuptake of norepinephrine, and (4) a direct smooth muscle effect. . . . Our data indicate that imipramine has a musculotropic relaxant effect which is more potent than that of flavoxate. This direct effect on bladder smooth muscle distal to the cholinergic receptor site . . . may be important mechanism responsible for the urologic efficacy of the drug." Imipramine was also „shown to reduce dog bladder and urethral pressure responses to pelvic nerve stimulation and a variety of other stimuli. (Creed, et al., *Brit. J. Urol.*, 54, 5 (1982)). These authors concluded that this agent "was acting selectively as a local anesthetic agent." The authors also stated that "imipramine . . . is unlikely to block uptake of biogenic amines" based upon their failure to see augmentation of responses to norepinephrine. Imipramine also induced a suppression of potassium-induced contraction of guinea pig bladder muscle strips in vitro; atropine and lidocaine were not effect at high concentration. (Noronha-Blob, et al., supra).

Imipramine has been found to inhibit norepinephrine reuptake. Imipramine potentiated the effects of hypogastric nerve stimulation on cat bladder relaxation in vivo (Shaffer, et al., *Neuropharm.*, 18, 33 (1979)). These effects were considered to be evidence of uptake inhibition at catecholaminergic terminals at the bladder. Imipramine also enhanced the in vitro relaxation effects of norepinephrine on dog bladder muscle strips but had no effects alone. (Lipshultz, et at., *Invest. Urol.*, 11, 182 (1973)). These results indicate that the effects of imipramine are indirect and mediated through the catecholinergic innervation of the bladder. Imipramine has also been shown to increase urethral pressure in female dogs and this effect could be suppressed by phenoxybenzamine (Khanna, et al., *Urology*, 6, 48 (1975)).

Imipramine has also been shown to inhibit the reuptake of serotonin (5-HT). The administration of imipramine increased the threshold for activating the bladder-spinal-bladder (vesicovesical) micturition reflex but had no effect on supraspinal reflex or myogenic activity of bladder with acute administration. The repeated administration of imipramine increased threshold for supraspinal reflex. Treatment with PCPA (a serotonin depleting agent) decreased acute treatment but not repeated treatment effects. (Maggi, et al., *J. Pharm. Exp. Ther.*, 248, 278 (1988)).

In addition to the role of norepinephrine in lower urinary tract physiology, serotonergic neurons and receptors have also been shown to have effects on lower urinary tract function. These effects include the inhibition of detrusor contractile activity and the reflex responses to distension of the bladder wall by altering the threshold to sensory stimuli (Thor, et al., *Development Brain Res.*, 54, 35 (1990); de Groat and Ryall, *Exp. Brain Res.*, 3, 299 ( 1967); McMahon and Spillane, *Brain Res.*, 234, 237 (1982)).

From the above, it is apparent that while imipramine and other tricyclic antidepressants are used to treat a variety of lower urinary tract disorders, the predominant mechanism responsible for these clinical effects remains unclear. Clearly these compounds have multiple mechanisms. However, which mechanism primarily responsible for any of the mentioned utilities is subject to continuing experimentation and discussion. Based upon such experimental evidence, B. D. Schmidtt, in a review article entitled "Nocturnal enuresis: An update on treatment" (*Pediatr. Clin, N. Amer.*, 29, 21 (1982)), stated "The mechanism of action [of imipramine] seems to be largely its anti-cholinergic effect". H. G. Rushton, in his review entitled "Nocturnal enuresis: Epidemiology, evaluation and currently available treatment: options" (*J. Pediatr.*, 114, 691 (1989)), stated "Imipramine has also been shown to exert peripheral anticholinergic and antispasmodic effects, as well as to have complex effect on sympathetic input to the bladder". L. M. D. Shortliffe and T. A. Stamey, in their chapter in the text *Campbell's Urology* entitled "Urinary incontinence in the female—Stress urinary incontinence" stated "Imipramine . . . It is a dibenzazepine derivative that has some anticholinergic activity and is useful for treating childhood enuresis. Although the drug's mechanism of stopping enuresis is unknown, it is thought to suppress abnormal detrusor contractions and potentiate urethral α-adrenergic activity".

Thus, the literature is, at best, uncertain as to the biological mechanism underlying the ability for the tricyclic antidepressants to treat incontinence. Moreover, it is clear that to the extent that any one or combination of these mechanisms may be useful for producing the end result, the compounds also have mechanisms which result in undesirable side effects. As noted above, imipramine and the other tricyclic antidepressants do possess a strong anticholinergic effect which likely results in the aforementioned side effects. Not only are such side effects annoying, but they may limit the effectiveness or even the use of such drugs. Accordingly, the need to discover drugs useful for treating incontinence without such side effects is evident.

SUMMARY OF THE INVENTION

The present invention provides a method of treating lower urinary tract disorders employing compounds which inhibit norepinephrine (NE) reuptake and which have a negligible anticholinergic effect. As defined further below, such compounds have an in vitro NE reuptake inhibition IC$_{50}$ of no greater than 50 nM and ratio of in vitro anti-cholinergic receptor binding assay IC$_{50}$ to NE reuptake inhibition assay IC$_{50}$ of at least 10.

DETAILED DESCRIPTION AND PREFERRED EMBODIMENT

The present invention provides a method for treating lower urinary tract disorders employing "pure" reuptake inhibitors. The term "pure" in this regard refers to compounds whose NE activity is relatively potent and considerably greater than any anticholinergic effect. The potency of the norepinephrine and anticholinergic effect is determined by the following test systems.

In vitro inhibition of NE reuptake in synaptosomes and $^3$H-QNB ligand displacement assays are performed as disclosed by Wong, et al., *J. Pharm. Exp. Therap.*, 222, 61 (1982).

The NE uptake assay is otherwise referred to herein as the in vitro NE reuptake assay while the $^3$H-QNB ligand displacement assay is otherwise referred to as the in vitro anti-cholinergic assay.

Using the test systems noted above, skilled artisans can evaluate any compound and determine the $IC_{50}$, i.e., the molar concentration for which each compound is 50% effective in each of the test systems. By performing these simple tests, one can determine the $IC_{50}$ in each of these systems and then determine whether such compounds would be particularly useful for treating lower urinary tract disorders according to the following two criteria:

(1) The NE reuptake $IC_{50}$ cannot be greater than 50 nM;

(2) The ratio of the anticholinergic $IC_{50}$ to NE $IC_{50}$ must be at least 10.

Subject to the above criteria, compounds disclosed in the following references can be employed in the method of this invention:

Aryloxypropylamine compounds as found in U.S. Pat. No. 4,313,896:

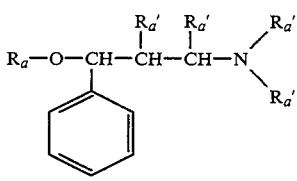

wherein:

each $R_a'$ is independently hydrogen or methyl; wherein $R_a$ is naphthyl or

wherein:

$R_a''$ and $R_a'''$ are halo, trifluoromethyl, $C_1-C_4$ alkyl, $C_1-C_3$ alkoxy or $C_3-C_4$ alkenyl; and wherein each m is 0, 1 or 2; and pharmaceutically acceptable acid addition salts thereof;

Aryloxypropylamine compounds as found in U.S. Pat. No. 4,956,388:

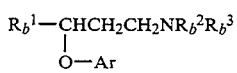

wherein:

$R_b^1$ is $C_5-C_7$ cycloalkyl, thienyl, halothienyl, ($C_1-C_4$ alkyl)thienyl, furanyl, pyridyl or thiazolyl; Ar is

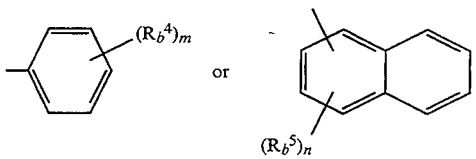

each of $R_b^2$ and $R_b^3$ independently is hydrogen or methyl;

each $R_b^4$ independently is halo, $C_1-C_4$ alkyl, $C_1-C_3$ alkoxy or trifluoromethyl;

each $R_b^5$ independently is halo, $C_1-C_4$ alkyl or trifluoromethyl;

m is 0, 1 or 2;

n is 0 or 1; and the pharmaceutically acceptable acid addition salts thereof; and 1-phenyl-3-naphthalenyloxypropanamine compounds as found in EPO Patent Application Publication 288,188:

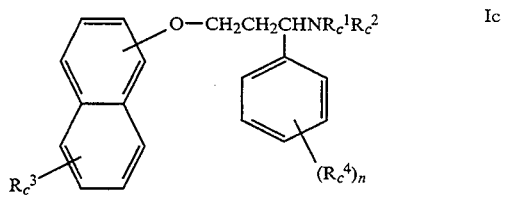

wherein:

each of $R_c^1$ and $R_c^2$ independently is hydrogen or methyl;

$R_c^3$ is hydrogen, halo, $C_1-C_4$ alkyl, $C_1-C_3$ alkoxy or trifluoromethyl;

each $R_c^4$ independently is hydrogen, halo, $C_1-C_4$ alkyl, $C_1-C_3$ alkoxy or trifluoromethyl;;

n is 1 or 2;

when n is 2, each $R_c^4$ can be combined to form methylenedioxy; or a pharmaceutically acceptable acid addition salt thereof.

The compounds as drawn above and as employed in the present invention include all individual enantiomers, pharmaceutically acceptable salts, and/or solvates of such compounds. The aforementioned references describing compounds Ia, Ib, and Ic are expressly incorporated by reference into this application. The substituent groups disclosed above are the same as used in the respective references except that the R-substituents are subscripted by a, b, or c as noted and the m and n definitions are used to be consistent with all three groups of compounds.

Of particular interest from the above compounds is the compound tomoxetine. Tomoxetine is chemically known as (-)-N-methyl-3-(2-methylphenoxy)-3-phenylpropylamine. Tomoxetine hydrochloride has been evaluated clinically to evaluate its antidepressant and antiobesity potential. Tomoxetine has an NE reuptake inhibition $IC_{50}$ of 1.9+0.4 nM and anticholinergic $IC_{50}$ of 21 μM and therefore falls well within the criteria defined above for use in treating lower urinary tract disorders. In addition, the following observations are consistent with tomoxetine's ability to treat incontinence:

During clinical evaluation of tomoxetine and imipramine as potential treatments for depression, one noted side effect for both compounds was that of urine retention. However, tomoxetine was reported to have considerably fewer side effects such as dry mouth, drowsiness, and dizziness which is likely associated with the anticholinergic effects of imipramine. Similarly, in the cat, tomoxetine was demonstrated as increasing bladder capacity and decreasing the amplitude and frequency of contractions.

In in vitro systems, tomoxetine and imipramine have been shown to increase NE release in dog and rabbit urethra and bladder fragments. Tomoxetine has also been shown to significantly increase the contractile response of rat urethral tissue to NE and to augment the relaxation of rat bladder tissue to NE. These effects are in agreement with the known properties of NE reuptake inhibitors.

The amount of compound required to effectively treat incontinence will depend upon the compound employed and its relative potency for effecting monoamine reuptake inhibition. Such doses can be generally extrapolated based upon the in vitro and any in vivo testing such as that mentioned above. For example, for adult patients, tomoxetine would be expected to be effective when administered in amounts of 20–200 milligrams per day. However, it should be readily understood that the amount of the compound actually administered will be determined by a physician, in light of all the relevant circumstances including the particular condition to be treated, the choice of compound to be administered, and the choice of route of administration.

The compounds employed in the present invention may be administered by the oral and rectal routes, topically, parenterally, e.g., by injection and by continuous or discontinuous intra-arterial infusion; in the form of, for example, tablets, lozenges, sublingual tablets, sachets, cachets, elixirs, gels, suspensions, aerosols, ointments, for example, containing from 1 to 10% by weight of the active compound in a suitable base, soft and hard gelatin capsules, suppositories, injectable solutions and suspensions in physiologically acceptable media, and sterile packaged powders adsorbed onto a support material for making injectable solutions. Advantageously for this purpose, compositions may be provided in dosage unit form, preferably each dosage unit containing from about 5 to about 500 mg of the indicated compound. Dosages from about 0.5 to about 300 mg/kg per day, preferably 0.5 to 20 mg/kg, of active ingredient will be typical subject to the criteria and admonitions listed above.

The formulations employed in the present invention normally will consist of at least one compound as defined mixed with a carrier, or diluted by a carrier, or enclosed or encapsulated by an ingestible carrier in the form of a capsule, sachet, cachet, paper or other container or by a disposable container such as an ampoule. A carrier or diluent may be a solid, semi-solid or liquid material which serves as a vehicle, excipient or medium for the active therapeutic substance.

Some examples of the diluents or carrier which may be employed in such pharmaceutical compositions are lactose, dextrose, sucrose, sorbitol, mannitol, propylene glycol, liquid paraffin, white soft paraffin, kaolin, fumed silicon dioxide, microcrystalline cellulose, calcium silicate, silica, polyvinylpyrrolidone, cetostearyl alcohol, starch, modified starches, gum acacia, calcium phosphate, cocoa butter, ethoxylated esters, oil of theobroma, arachis oil, alginates, tragacanth, gelatin, syrup, methyl cellulose, polyoxyethylene sorbitan monolaurate, ethyl lactate, methyl and propyl hydroxybenzoate, sorbitan trioleate, sorbitan sesquioleate and oleyl alcohol and propellants such as trichloromonofluoromethane, dichlorodifluoromethane and dichlorotetrafluoroethane. In the case of tablets, a lubricant may be incorporated to prevent sticking and binding of the powdered ingredients in the dies on the, punch of the tableting machine. For such purpose there may be employed for instance aluminum, magnesium or calcium stearates, talc or mineral oil.

Preferred pharmaceutical forms employed in the present invention are capsules, tablets, suppositories, injectable solutions, creams and ointments. Especially preferred are formulations for oral ingestion.

I claim:

1. A method of treating urinary incontinence comprising administering to a human suffering from urinary incontinence an effective amount of tomoxetine or a pharmaceutically acceptable salt thereof.

2. A method of claim 1 wherein the incontinence is both urge incontinence and stress incontinence.

3. A method of claim 2 wherein the patient is a woman of childbearing age.

4. A method of claim 2 wherein the patient is an elderly person.

5. A method of claim 2 wherein the patient is a child and the incontinence is nocturnal enuresis.

6. A method of claim 1 wherein the incontinence is urge incontinence.

7. A method of claim 6 wherein the patient is a woman of childbearing age.

8. A method of claim 6 wherein the patient is an elderly person.

9. A method of claim 6 wherein the patient is a child and the incontinence is nocturnal enuresis.

10. A method of claim 1 wherein the incontinence is stress incontinence.

11. A method of claim 10 wherein the patient is a woman of childbearing age.

12. A method of claim 10 wherein the patient is an elderly person.

13. A method of claim 10 wherein the patient is a child and the incontinence is nocturnal enuresis.

* * * * *